(12) United States Patent
Wald et al.

(10) Patent No.: US 9,211,082 B2
(45) Date of Patent: Dec. 15, 2015

(54) METHOD FOR MAGNETIC RESONANCE IMAGING USING SATURATION HARMONIC INDUCED ROTARY SATURATION

(75) Inventors: Lawrence L Wald, Cambridge, MA (US); Bo Zhu, Cambridge, MA (US); Bruce R Rosen, Lexington, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 215 days.

(21) Appl. No.: 13/537,518

(22) Filed: Jun. 29, 2012

(65) Prior Publication Data

US 2013/0178734 A1  Jul. 11, 2013

Related U.S. Application Data

(60) Provisional application No. 61/503,018, filed on Jun. 30, 2011.

(51) Int. Cl.
*A61B 5/055* (2006.01)
*G01R 33/56* (2006.01)
*G01R 33/561* (2006.01)

(52) U.S. Cl.
CPC ............ *A61B 5/055* (2013.01); *G01R 33/5601* (2013.01); *G01R 33/5616* (2013.01)

(58) Field of Classification Search
CPC . A61B 5/055; G01R 33/5601; G01R 33/5616
See application file for complete search history.

(56) References Cited

U.S. PATENT DOCUMENTS

| | | | |
|---|---|---|---|
| 5,099,206 | A | 3/1992 | Imaizumi et al. |
| 5,170,120 | A | 12/1992 | Barbara et al. |
| 5,944,663 | A | 8/1999 | Kuth et al. |
| 6,486,669 | B1 | 11/2002 | Sinkus et al. |

(Continued)

FOREIGN PATENT DOCUMENTS

WO   2008064322 A1   5/2008

OTHER PUBLICATIONS

Antti Markkola, Academic Dissertation, To be presented with the permission of the Faculty of Medicine of the University of Helsinki, for public discussion in Auditorium XIII on Oct. 31, 2003, at 12 noon.*

(Continued)

*Primary Examiner* — Bo J Peng
(74) *Attorney, Agent, or Firm* — Quarles & Brady, LLP

(57) ABSTRACT

A system and method for producing an image of a subject with a magnetic resonance imaging system, in which the image depicts an image contrast indicative of rotary saturation produced in response to magnetic particles administered to the subject, are provided. An agent that includes magnetic particles is administered to the subject. An electromagnetic drive field is applied to the subject at a drive frequency so that the magnetic particles produce magnetic fields that oscillate at the drive frequency and harmonics thereof. A spin-lock field is then established at a spin-lock frequency that is a harmonic of the drive frequency in order to produce rotary saturation of nuclear spins affected by the magnetic fields produced by the magnetic particles. Image data is then acquired from the subject using the MRI system, from which an image of the subject that depicts an image contrast indicative of the produced rotary saturation is reconstructed.

14 Claims, 3 Drawing Sheets

(56) References Cited

U.S. PATENT DOCUMENTS

| | | |
|---|---|---|
| 6,836,114 B2 | 12/2004 | Reddy et al. |
| 6,841,995 B2 | 1/2005 | Weitekamp |
| 7,025,253 B2 | 4/2006 | Sinkus et al. |
| 7,115,094 B2 | 10/2006 | Azuma et al. |
| 7,956,613 B2 | 6/2011 | Wald |
| 2008/0255444 A1 | 10/2008 | Li |
| 2008/0281183 A1 | 11/2008 | Wald et al. |
| 2009/0123384 A1 | 5/2009 | Wald et al. |
| 2010/0176810 A1 | 7/2010 | Bolster, Jr. |
| 2010/0267781 A1 | 10/2010 | Pellechia |

OTHER PUBLICATIONS

Alford, et al., Delta Relaxation Enhanced MR: Improving Activation—Specificity of Molecular Probes Through R1 Dispersion Imaging, Magnetic Resonance in Medicine, 2009, 61:796-802.

Biederer, et al., Magnetization Response Spectroscopy of Superparamagnetic Nanoparticles for Magnetic Particle Imaging, Journal of Physics D: Applied Physics, 2009, 42, 205007, 7 pages.

Gleich, et al., Tomographic Imaging Using the Nonlinear Response of Magnetic Particles, Nature, 2005, 435:1214-1217.

International Commission on Non-Ionizing Radiation Protection, ICNIRP Statement: Guidance on Determining Compliance of Exposure to Pulsed and Complex Non-Sinusoidal Waveforms Below 100 KHZ with ICNIRP Guidelines, Health Physics, 2003, 84(3):383-387.

Redfield, Nuclear Magnetic Resonance Saturation and Rotary Saturation in Solids, Physical Review, 1955, 98:1787-1809.

Witzel, et al., Stimulus-Induced Rotary Saturation (SIRS): A Potential Method for the Detection of Neuronal Currents with MRI, Neuroimage, 2008, 42(4):1357-1365.

\* cited by examiner

METHOD FOR MAGNETIC RESONANCE IMAGING USING SATURATION HARMONIC INDUCED ROTARY SATURATION

CROSS-REFERENCE TO RELATED APPLICATIONS

This application claims the benefit of U.S. Provisional Patent Application Ser. No. 61/503,018 filed on Jun. 30, 2011, and entitled "Method for Magnetic Resonance Imaging Using Saturation Harmonic Induced Rotary Saturation."

STATEMENT REGARDING FEDERALLY SPONSORED RESEARCH

This invention was made with government support under RR014075 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for imaging magnetic particles with MRI.

In recent years, a method has been proposed for administering magnetic particles, such as super paramagnetic iron oxide ("SPIO"), that serve as a contrast medium into a subject and forming an image of a distribution of the contrast medium. Such methods are referred to as magnetic particle imaging ("MPI"). MPI differs from conventional MRI in many ways. First and foremost, MPI relies on a unique imaging system that is different than conventional MRI systems. Also, in MPI, an image of the distribution of magnetic particles within a subject is formed by measuring a change in the voltage induced in a detection coil as a driving magnetic field magnetizes the particles in a non-linear fashion.

In MRI, magnetic contrast agents are generally visualized by way of their effect on the relaxation times $T_1$, $T_2$, and $T_2^*$. For example, magnetic contrast agents may shorten the $T_1$ of those nuclear spins near to the contrast agent, thereby altering the signal detected from those nuclear spins and producing a contrast mechanism.

A method for modulating the contrast achieved by an MRI contrast agent referred to as "dreMR" is taught by J. K. Alford, et al., in "Delta Relaxation Enhanced MR: Improving Activation-Specificity of Molecular Probes through R1 Dispersion Imaging," *Magnetic Resonance in Medicine*, 2009; 61(4):796-802. The dreMR method achieves this contrast modulation because for rapidly tumbling paramagnetic agents the longitudinal relaxation time, $T_1$, which is the reciprocal of the longitudinal relaxation rate, $R_1$, varies little over the range 1.2-1.8 Tesla ("T"), while slowly tumbling, bound species elicit a steep dependence of $T_1$ relaxation over the same field range. Using the dreMR method, comparisons of images undergoing relaxation at different field strengths allows direct separation of the relaxation effects of the free versus the bound pools as well as allowing subtraction of the two images. In dreMR, both the background tissue and the free contrast agent pool are subtracted out. While clinical MRI systems have a fixed field strength, such as 1.5 T, it is feasible to build and operate an insert compatible with clinical MRI systems that can produce enough change in the $B_0$ field to significantly modulate the relaxation of bound contrast agents.

In light of the foregoing, it would be advantageous to provide a system and method for acquiring contrast-enhanced images of a subject that has been administered a magnetic particle contrast agent. Such a system and method would preferably utilize a conventional, clinical MRI system, rather than require a unique imaging system (as required for MPI) or a significant modification to a standard MRI system (as required for dreMR). The benefits of being able to utilize a clinical MRI system include improving MPI by allowing spatial encoding to be done by MRI rather than inductive pick-up or altering an external static magnetic field, thereby improving spatial resolution and imaging quality than current MPI. It would also be beneficial to image a contrast agent by a means other than the contrast agent's effect on the conventional $T_1$, $T_{1\rho}$, $T_2$, or $T_2^*$ relaxation characteristics because natural variations in these characteristics in the subject may need to be distinguished from the effect of the contrast agent.

SUMMARY OF THE INVENTION

The present invention overcomes the aforementioned drawbacks by providing a method for producing an image of a subject with an MRI system, in which the image depicts an image contrast indicative of the rotary saturation produced in response to magnetic particles administered to the subject. A contrast agent that includes magnetic particles is administered to the subject. An electromagnetic drive field is applied to the subject at a drive frequency so that the magnetic particles produce local magnetic fields that oscillate at the drive frequency and harmonics thereof. The drive field is applied simultaneously with a spin-lock field that is established at a spin-lock frequency that is a harmonic of the drive frequency. The oscillating magnetic field produced by the contrast agent at the spin-lock frequency produces rotary saturation of nuclear spins in the spin-locked condition, thereby rotating the spin-locked magnetization vector away from the spin-lock $B_1$-field. Image data is then acquired from the subject using the MRI system, from which an image of the subject that depicts an image contrast indicative of the produced rotary saturation is reconstructed. This image can be compared to data acquired without applying the electromagnetic drive field, or acquired with the spin-lock frequency off-resonance with the harmonic of the drive frequency. Subtraction of the image and this data produces an image representative of the effects from the magnetic particles and not intensity variations from other sources.

It is an aspect of the invention to provide a method for directing an MRI to acquire image data from a subject that contains magnetic particles. The method includes directing the MRI system to perform a pulse sequence that includes a spin-locking preparatory portion and a data acquisition portion. The spin-locking preparatory portion includes an external driving electromagnetic field, which may be in the audio frequency range, having a drive frequency that, when applied to the magnetic particles, causes the magnetic particles to generate a time-varying electromagnetic field. Because the magnetization of the particles is a non-linear function of the applied electromagnetic drive field, the magnetization of the particles will produce time-varying fields at the drive frequency and also at the harmonics of that frequency. The spin-locking preparatory portion includes a radio frequency ("RF") spin-locking electromagnetic field having an amplitude such that the resonance frequency for excitation in the rotating frame is equal to a harmonic of the drive frequency. Additionally, the spin-lock preparatory portion may have a first RF field preceding the spin-locking electromagnetic field, and may also have a second RF field following the spin-locking electromagnetic field that acts to return the spin-locked magnetization to the longitudinal axis for sampling by an imaging sequence.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A method for magnetic resonance imaging ("MRI") that is capable of differentially detecting the presence of magnetic particles in a subject using an MRI system is provided. Typically, contrast agents are visualized with MRI through their effect on the water relaxation times: $T_1$, $T_{1\rho}$, $T_2$, or $T_2^*$. Rather than looking for conventional relaxation time changes associated with the magnetic particles, the provided method produces images affected by the non-linear response of the magnetic particles to an externally applied sinusoidal electromagnetic field. The magnetization produced by the magnetic particles in response to this "drive field" affects the local magnetic fields in the subject, and this effect is measured using a rotary saturation technique.

Figure 1A:
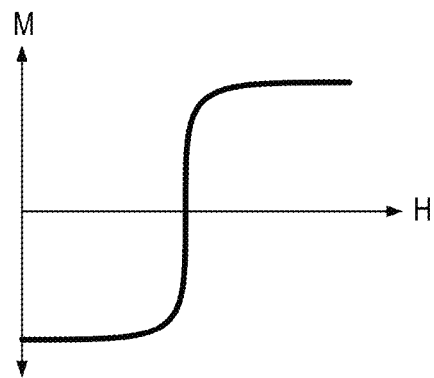
FIG. 1A is an example plot of a magnetic particle magnetization response to an externally applied magnetic field.
Figure 1B:
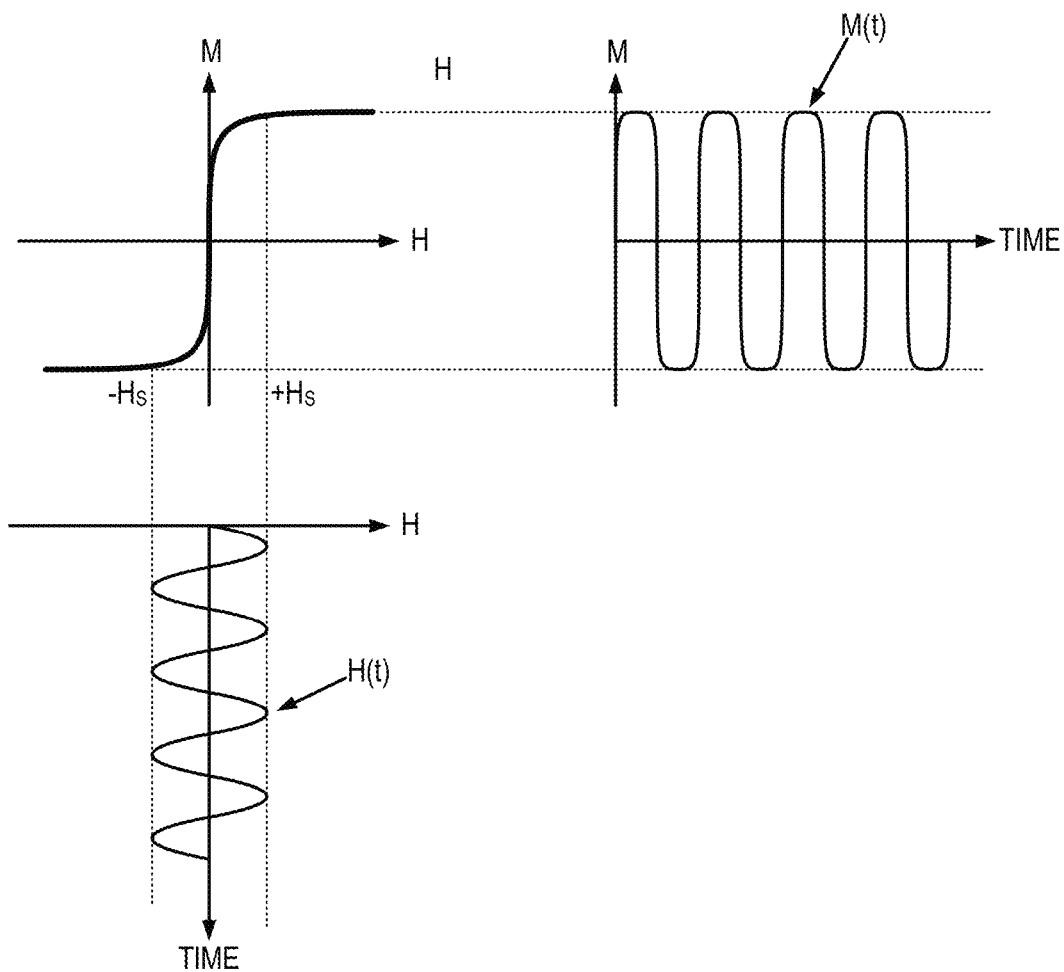
FIG. 1B is a graphic illustration of the effect of an externally applied, time-varying magnetic field on the magnetization of a magnetic particle.

In traditional magnetic particle imaging ("MPI"), the magnetic particles are not detected with conventional MRI techniques; rather, they are driven with a sinusoidal driving field, and their response field at a harmonic frequency is detected through inductive pickup. Note that it is difficult to detect the particles' response at the drive frequency due to the presence of the drive field itself at this frequency. The magnetization of the magnetic particles exhibits a non-linear response to the driving field, in which magnetization responds linearly at low magnetic field strengths, and is saturated at high magnetic field strengths. FIG. 1A shows the variation of the magnetization, M, of a magnetic particle, such as a super paramagnetic iron oxide ("SPIO") particle, as a function of magnetic field strength, H, at the location of the magnetic particle. It can be seen that the magnetization, M, becomes saturated and, therefore, no longer changes, outside of a range of magnetic field values, $-H_S, \ldots, +H_S$. FIG. 1B illustrates the effect of a sinusoidal magnetic field, H(t), at the location of the magnetic particle where the amplitude of the magnetic field, H(t), falls within the range of magnetic field strengths, H, that do not result in a saturated magnetization, M. In this instance, the magnetization, M, of the particle oscillates between its saturation values at the frequency of the magnetic field, H(t). The resultant time-varying magnetization, M(t) is illustrated on the right-hand side of FIG. 1B. The time-varying magnetization, M(t), produced by the magnetic particles in response to a driving magnetic field, H(t), contains harmonics of the driving field frequency. In conventional MPI, the field at one or more harmonic frequencies is detected through standard inductive pickup, for example, by using a tuned LC circuit.

In the provided method, the direct detection of magnetic particles used in MPI is replaced with the detection of harmonic fields through their resonant interaction with the nuclear spins encoded in an MR image. Thus, in general, an imaging method that renders the water nuclei detected by MRI to be resonantly sensitive to the harmonic frequencies generated by the magnetic particles in response to an external drive field is provided. To elicit this sensitivity, the principles of rotary saturation are employed. The magnetic particles may be localized by way of image intensity changes associated with the magnetic fields induced at the harmonic frequencies by the magnetic particles. This method provides the flexibility of MR image encoding to MPI, or, conversely, provides a new mechanism for a magnetic contrast agent to alter the intensity locally in an MR image.

The magnetic resonance principle of rotary saturation is a phenomena described for solids and liquids by A. G. Redfield in "Nuclear Magnetic Resonance Saturation and Rotary Saturation in Solids," *Phys. Rev.*, 1955; 98:1787-1809. The rotary saturation effect manipulates nuclear spin magnetization while it is rendered stationary, or "spin-locked," in the rotating frame-of-reference. In MRI spin-locking methods, the equilibrium magnetization along the z-axis, coinciding with the static magnetic field, $B_0$, is first tipped by a ninety degree RF pulse into the transverse x-y plane. Once in the transverse plane, the magnetization may be viewed as being stationary in the frame-of-reference with which it rotates (the rotating frame). A second resonant RF field is subsequently applied along the direction of the magnetization in the rotating frame. While this "spin-locking electromagnetic field," $B_{1,lock}$, is being applied, the magnetization may be viewed as being stationary in the rotating frame because it is aligned along $B_{1,lock}$, which is also stationary in the rotating frame. Thus, the rotating frame picture may be perceived as being in "equilibrium." The magnitude of the spin-locked magnetization is observed by turning off the spin-locking field, $B_{1,lock}$, and measuring the amplitude of the resulting free induction decay ("FID"). In the alternative, the spin-locking field, $B_{1,lock}$, can be turned off and the magnetization in the transverse plane flipped back up to the z-axis by a second ninety degree RF pulse for subsequent sampling with conventional MRI data acquisition methods. In the latter approach, the spin-locking period is referred to as a "spin-lock preparation."

Because the spin-locked magnetization is created by the main magnetic field, $B_0$, it is much larger than the small spin-locking field, $B_{1,lock}$, field would be able to create through true Boltzmann polarization. Thus, the spin-locked magnetization is in equilibrium in direction, but not in magnitude. As a result, this magnetization will eventually relax to a much smaller value, but still be aligned along $B_{1,lock}$. This relaxation in the rotating frame has a characteristic time, $T_{1\rho}$. Typical values for $T_{1\rho}$ in vivo are hundreds of milliseconds, so the spin-locked state can last for several hundred milliseconds without substantial loss of magnetization. The mechanisms for $T_{1\rho}$ relaxation are analogous to normal $T_1$ relaxation: random magnetic fields fluctuating at the Larmor frequency and orthogonal to the equilibrium magnetization. However, while fluctuating fields in the plane transverse to the main magnetic field, $B_0$, cause $T_1$ relaxation in conventional MR imaging methods, fluctuating fields in the plane transverse to the spin-locking field, $B_{1,lock}$, cause $T_{1\rho}$ relaxation in spin-lock MRI. Because the equivalent of the Larmor precession frequency in the spin-locked state is proportional to the spin-locking electromagnetic field, $B_{1,lock}$, the proper frequency for efficient saturation of the magnetization is orders of magnitude lower in frequency than that needed for normal $T_1$ relaxation.

In the spin-locked state, nuclear spins experience longitudinal and transverse relaxation from external magnetic fields, characterized by the relaxation constants $T_{1\rho}$ and $T_{2\rho}$. In one embodiment of the present invention, the external magnetic fields that are responsible for the $T_{1\rho}$ and $T_{2\rho}$ relaxation are created by time-varying magnetization generated by magnetic particles responding to an externally applied time-varying electromagnetic field.

The Larmor frequency of the spin-locked nuclear spins in the rotating frame, $\omega_{SL}$ is given by:

$$\omega_{SL} = \gamma B_{1,lock} \quad (1);$$

where $\gamma$ is the gyromagnetic ratio of the nuclear spin species to be imaged, and $B_{1,lock}$ is the applied spin-locking electromagnetic field. The amplitude of the spin-locking field, $B_{1,lock}$, is set to produce oscillations in external magnetic fields at the "spin-lock resonant frequency,"$\omega_{SL}$.

An alternate view of rotary saturation is to view the rotary saturation field as a field that excites nuclear spins in the rotating frame. In effect, the rotary saturation field serves to resonantly rotate the spin-locked magnetization away from the $B_{1,lock}$ field in an analogous manner to the way that an RF field causes excitation by rotating longitudinal magnetization away from the $B_0$ field. When rotated away from the spin-lock field, the application of a ninety-degree "flip-back" RF pulse can be applied to return either the magnetization remaining along the $B_{1,lock}$ field back to the z-axis for subsequent quantification by an imaging sequence, or the component orthogonal to $B_{1,lock}$. This choice may be made by adjusting the phase of the flip-back pulse. Magnetization not along the desired direction will be dephased by application of a dephasing gradient, or by $T_2^*$ relaxation.

The provided method uses the fluctuating magnetic fields associated with magnetic particles driven with an external drive field, $B_{drive}$, at frequency, $\omega_{drive}$, to generate harmonic fields at frequencies, $n \cdot \omega_{drive}$, where n is an integer that indicates the harmonic. By matching the spin-lock resonance frequency, $\omega_{SL}$, to a harmonic of the drive field frequency, such as the second harmonic, $2 \cdot \omega_{drive}$, images that are resonantly sensitive to the magnetic particles can be acquired. Because the image intensity will be reduced where the rotary saturation occurs (if the component parallel to $B_{1,lock}$ is flipped-back), the locations where both the magnetic particles are sufficiently dense, and where the driving field is of sufficient amplitude and frequency, will produce a contrast mechanism indicative of the magnetic particle contrast agent. A positive contrast is produced by choosing to flip back the component orthogonal to $B_{1,lock}$. In this instance, the locations of the contrast agent will appear bright against a dark background.

An exemplary drive field, $B_{drive}$, may be a 0.5 T amplitude field having a frequency, $\omega_{drive} = 100$ Hz. Such a drive field may yield a second harmonic from the contrast agent's magnetization versus the applied field saturation curve that is 17 decibels lower in power than the drive field. Because a 3 milligram iron per milliliter iron oxide suspension within a cylindrical capillary tube generates approximately a $1 \times 10^{-4}$ T field in the immediate vicinity outside the tube when placed in a 3 T field, it is contemplated that placing the same suspension in a 1.5 T scanner and imposing a 0.5 T drive field oscillating at 100 Hz will generate a pseudo-sinusoidal magnetization response from the iron oxide particles with amplitude $2.9 \times 10^{-6}$ T. Thus, the second harmonic in such a setup is anticipated to be approximately $4 \times 10^{-7}$ T. While very small, an oscillating magnetic field of this amplitude can be detected using the provided method, which is sensitive to fields as small as $1 \times 10^{-9}$ T (1 nT), as described by T. Witzel, at al., in "Stimulus-Induced Rotary Saturation (SIRS): A Potential Method for the Detection of Neuronal Currents with MRI,"*Neuroimage*, 2008; 42:1357-1365.

In the provided method, the time-varying magnetic fields produced when magnetic particles are driven by an external driving field at frequency, $\omega_{drive}$, are utilized as a rotary saturation field. It is important to note, however, that detection of this response directly at the driving field frequency, that is with $\omega_{SL} = \omega_{drive}$, is very difficult because the external driving field itself would produce a large rotary saturation effect. To address this problem, the spin-lock field is set so as to be sensitive to a harmonic of the drive field according to:

$$\omega_{SL} = n \cdot \omega_{drive} \quad (2);$$

where $\omega_{SL}$ is the frequency of the spin-locking RF field, $\omega_{drive}$ is the frequency of the RF driving field, and n is an integer indicating the $n^{th}$ harmonic. Preferably, the second harmonic, n=2, is selected because higher harmonics will exhibit lower fields.

Because the provided method detects the harmonics of the rotary saturation effect, the provided method may be referred to as saturation harmonic induced rotary saturation, or "SHIRS." Note that in the absence of magnetic particles, it is contemplated that no harmonic fields will be present because the materials in the human body are non-ferrous and have a linear magnetization response.

Figure 2:
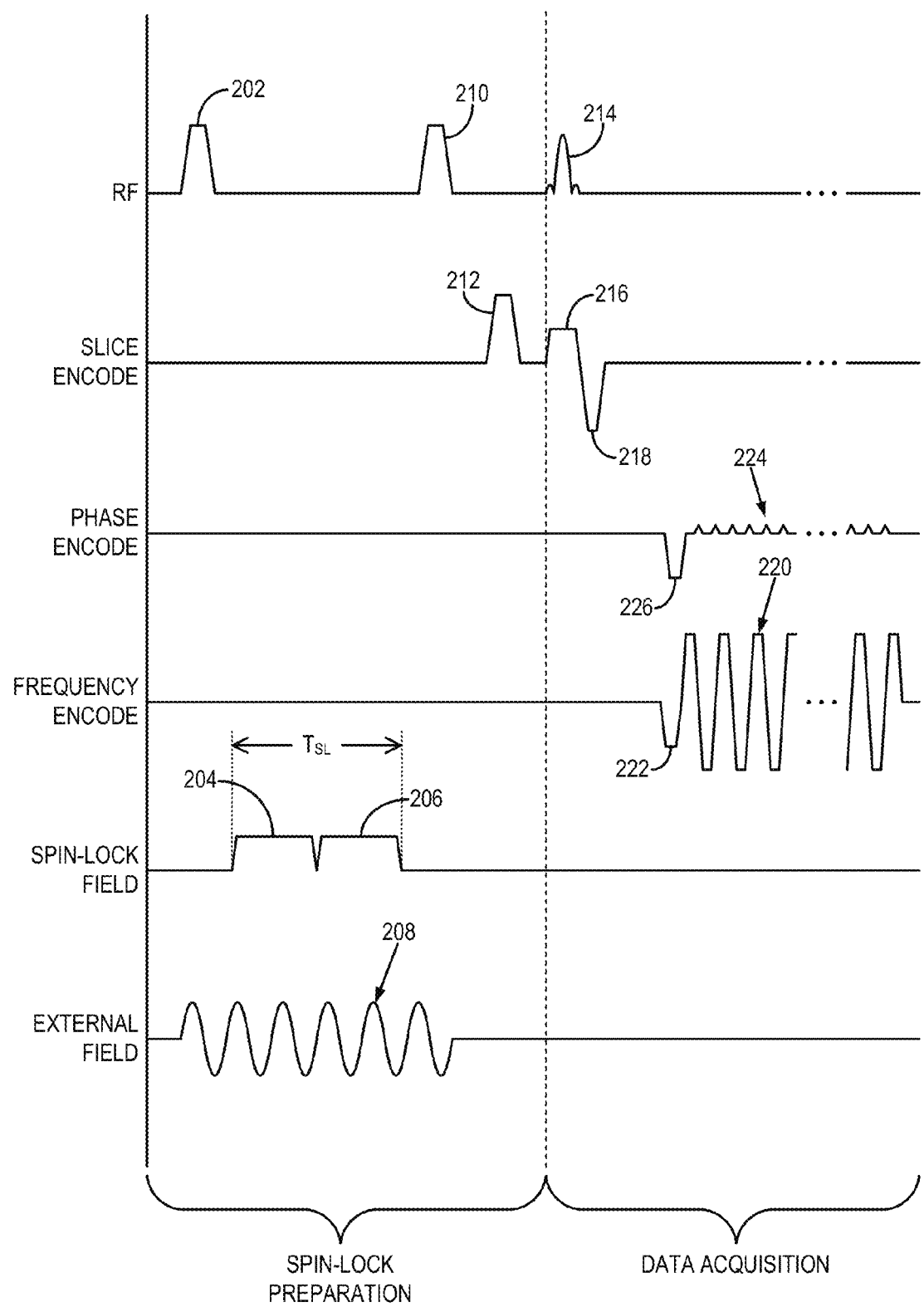
FIG. 2 is an example of a pulse sequence that includes a spin-locking preparatory portion and a data acquisition portion.

Referring now particularly to FIG. 2, an example of a pulse sequence that may be used to practice an embodiment of the present invention includes a spin-lock preparatory pulse sequence followed by a data acquisition pulse sequence, such as an echo-planar imaging ("EPI") pulse sequence. The spin-lock preparatory sequence includes a non-selective radio frequency ("RF") excitation pulse 202 that produces transverse magnetization in a subject. Subsequently, the spins producing the transverse magnetization are spin-locked in the transverse plane by the application of two, phase-alternating, spin-lock pulses 204, 206 for a duration of time, $T_{SL}$. The two spin-lock pulses 204, 206 are phase-shifted from the phase of the RF excitation pulse 202, for example, one by plus ninety degrees and the other by minus ninety degrees. By phase-alternating the spin-lock RF pulses 204, 206, image artifacts that would otherwise result from $B_1$ field inhomogeneities may be reduced. The amplitude of the spin-lock RF pulses 204, 206 determines the $B_{1,lock}$ field that is produced during the spin-locking condition. In the preferred embodiment, the amplitude is set such that the spin-locked Larmor frequency, $\omega_{SL} = \gamma B_{1,lock}$, is twice that of an externally applied drive field 208. As noted above, this externally applied drive field 208 is employed to induce oscillatory motion in magnetic particles administered to a subject.

Subsequent to the application of the spin-lock pulses 204, a second non-selective RF excitation pulse 210 is applied to restore the spin-locked magnetization to the longitudinal axis. The phase of this pulse may determine whether the component of the magnetization along $B_{1,lock}$, or whether the component orthogonal to $B_{1,lock}$ will be returned to the longitudinal axis. One or more spoiler gradients 212 are then applied to eliminate any residual transverse magnetization. The "$T_{1\rho}$-prepared" longitudinal magnetization, $M(T_{SL})$, remaining after the application of the spoiler gradients 212 is given by the equation:

$$M(T_{SL}) = M_0 e^{-\frac{T_{SL}}{T_{1\rho}}};\qquad(3)$$

where $M_0$ is the thermal equilibrium magnetization, $T_{SL}$ is the duration of the spin-lock pulses 204,206, and $T_{1\rho}$ is the longitudinal relaxation time in the rotating reference frame. When employing a spin-lock pulse sequence, the longitudinal magnetization is modulated, or weighted, by changes in the $T_{1\rho}$ of the tissues being imaged.

For imaging the $T_{1\rho}$-prepared signal, a gradient-echo EPI readout may be used, as illustrated in FIG. 2. In this data acquisition portion of the pulse sequence, an excitation pulse 214 is applied in the presence of a slice-selective gradient 216 to produce transverse magnetization in a slice through the subject. The excited spins are rephased by a rephasing gradient lobe 218, and then a time interval elapses before the data readout begins. A train of gradient-recalled echoes are produced by the application of an alternating readout gradient 220. The readout sequence begins with a negative readout gradient lobe 222, and the echo signals are produced as the readout gradient 220 oscillates between positive and negative values. Spatial encoding of the echoes is accomplished by a series of phase-encoding gradient blips 224, which are preceded by a prephasing gradient 226 that occurs before the echo signals are acquired to encode the first view with a negative k-space location. Subsequent phase-encoding blips 224 occur as the readout gradient 220 switches polarity. These phase-encoding blips 224 monotonically step the phase-encoding upward through k-space.

In one embodiment of the present invention, the EPI imaging pulse sequence is separate from the spin-lock magnetization preparation pulse sequence; however, it will be appreciated by those skilled in the art that many variations are possible. Other imaging pulse sequences can be employed after the spin-lock magnetization preparation pulse sequence, and the spin-lock magnetization preparation pulse sequence can be performed as an integral part of the imaging pulse sequence. In the latter case, the second RF pulse 210 and the spoiler gradient 212 are not required, and a separate RF excitation pulse is not required in the image acquisition pulse sequence that follows. In this embodiment, the imaging pulse sequence reads out the echo signals produced by the transverse magnetization at the completion of the spin-lock pulses 204,206.

Figure 3:
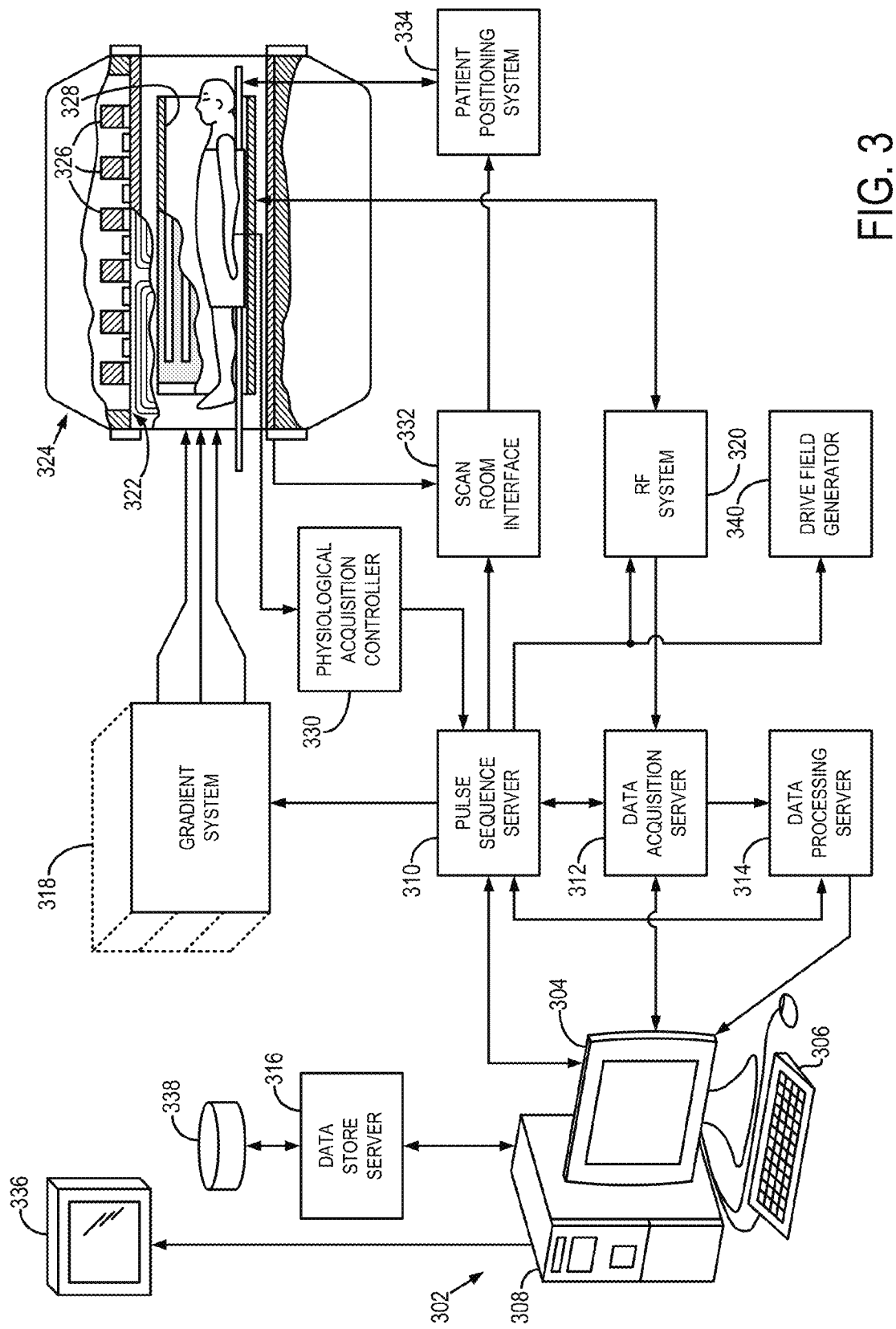
FIG. 3 is a block diagram of an example of a magnetic resonance imaging ("MRI") system that employs the present invention.

The foregoing method may be performed using an MRI system; thus, with reference now to FIG. 3, an exemplary MRI system 300 for practicing some embodiments of the invention is illustrated. The MRI system 300 includes a workstation 302 having a display 304 and a keyboard 306. The workstation 302 includes a processor 308, such as a commercially available programmable machine running a commercially available operating system. The workstation 302 provides the operator interface that enables scan prescriptions to be entered into the MRI system 300. The workstation 302 is coupled to four servers: a pulse sequence server 310; a data acquisition server 312; a data processing server 314, and a data store server 316. The workstation 302 and each server 310, 312, 314 and 316 are connected to communicate with each other.

The pulse sequence server 310 functions in response to instructions downloaded from the workstation 302 to operate a gradient system 318 and a radio frequency ("RF") system 320. Gradient waveforms necessary to perform the prescribed scan are produced and applied to the gradient system 318, which excites gradient coils in an assembly 322 to produce the magnetic field gradients $G_x$, $G_y$ and $G_z$ used for position encoding MR signals. The gradient coil assembly 322 forms part of a magnet assembly 324 that includes a polarizing magnet 326 and a whole-body RF coil 328.

RF excitation waveforms are applied to the RF coil 328, or a separate local coil (not shown in FIG. 3), by the RF system 320 to perform the prescribed magnetic resonance pulse sequence. Responsive MR signals detected by the RF coil 328, or a separate local coil (not shown in FIG. 3), are received by the RF system 320, amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the scan prescription and direction from the pulse sequence server 310 to produce RF pulses of the desired frequency, phase, and pulse amplitude waveform. The generated RF pulses may be applied to the whole body RF coil 328 or to one or more local coils or coil arrays (not shown in FIG. 3). A drive field generator 340 is used to generate the desired electromagnetic drive field. For example, the drive field generator may include an external solenoid, or a shielded solenoid, that is driven by a large amplifier at a low frequency. By way of example, an additional gradient amplifier can be utilized to drive the drive field generator.

The RF system 320 also includes one or more RF receiver channels. Each RF receiver channel includes an RF amplifier that amplifies the MR signal received by the coil 328 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2}\qquad(4);$$

and the phase of the received MR signal may also be determined:

$$\varphi = \tan^{-1}\left(\frac{Q}{I}\right).\qquad(5)$$

The pulse sequence server 310 also optionally receives patient data from a physiological acquisition controller 330. The controller 330 receives signals from a number of different sensors connected to the patient, such as electrocardiograph ("ECG") signals from electrodes, or respiratory signals from a bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized MR signal samples produced by the RF system 320 are received by the data acquisition server 312. The data acquisition server 312 operates in response to instructions downloaded from the workstation 302 to receive the real-time MR data and provide buffer storage, such that no data is lost by data overrun. In some scans, the data acquisition server 312 does little more than pass the acquired MR data to the data processor server 314. However, in scans that require information derived from acquired MR data to control the further performance of the scan, the data acquisition server 312 is programmed to produce such information and convey it to the pulse sequence server 310. For example, during prescans, MR data is acquired and used to calibrate the pulse sequence performed by the pulse sequence server 310. Also, navigator signals may be acquired during a scan and used to adjust the operating parameters of the RF system 320 or the gradient system 318, or to control the view order in which k-space is sampled. In all these examples, the data acquisition server 312 acquires MR data and processes it in real-time to produce information that is used to control the scan.

The data processing server 314 receives MR data from the data acquisition server 312 and processes it in accordance with instructions downloaded from the workstation 302. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 314 are conveyed back to the workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the workstation 302. The workstation 302 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a subject with a magnetic resonance imaging (MRI) system, the steps of the method comprising:
   a) administering to the subject, an agent that includes magnetic particles;
   b) applying an electromagnetic drive field to the subject at a drive frequency so that the magnetic particles produce magnetic fields that oscillate at the drive frequency and harmonics thereof;
   c) applying a spin-lock pulse to the subject that includes a spin-locking radio frequency (RF) pulse having a spin-lock frequency that is a harmonic other than a first harmonic of the drive frequency, the spin-lock pulse sequence producing rotary saturation of nuclear spins affected by the magnetic fields produced by the magnetic particles;
   d) acquiring image data from the subject using the MRI system following the application of the spin-lock pulse sequence; and
   e) reconstructing an image of the subject from the acquired image data, the reconstructed image depicting an image contrast indicative of the rotary saturation produced in step c).

2. The method as recited in claim 1 in which the spin-lock frequency is a second harmonic of the drive frequency.

3. The method as recited in claim 1 in which the magnetic particles include super paramagnetic iron oxide particles.

4. The method as recited in claim 1 in which the image contrast in the image reconstructed in step e) is related to a density of the magnetic particles.

5. The method as recited in claim 1 in which the image contrast in the image reconstructed in step e) is related to an amplitude of the electromagnetic drive field applied in step b).

6. The method as recited in claim 1 in which the electromagnetic drive field is applied contemporaneously with the spin-locking RF pulse in step c).

7. A magnetic resonance imaging (MRI) system, comprising:
   a magnet system configured to generate a polarizing magnetic field about at least a portion of a subject arranged in the MRI system;
   a plurality of gradient coils configured to apply a magnetic field gradient to the polarizing magnetic field;
   a radio frequency (RF) system including an RF coil configured to apply an RF field to the subject and to receive magnetic resonance signals therefrom;
   a drive field generator configured to generate an electromagnetic field;
   a computer system programmed to:
   direct the drive field generator to apply a driving electromagnetic field having a drive frequency that when applied to magnetic particles present in the subject, causes the magnetic particles to generate a time-varying electromagnetic field;
   direct the RF system to apply a spin-locking electromagnetic field having a frequency equal to a harmonic other than a first harmonic of the drive frequency, such that spin-locked magnetization is produced; and
   direct the RF system and the plurality of gradient coils to perform a pulse sequence to acquire k-space data by sampling magnetic resonance signals indicative of the spin-locked magnetization as it is affected by the time-varying electromagnetic field.

8. The MRI system as recited in claim 7 in which the frequency of the spin-locking electromagnetic field is a second harmonic of the drive frequency.

9. The MRI system as recited in claim 7 in which the magnetic particles include super paramagnetic iron oxide particles.

10. The MRI system as recited in claim 7 in which the computer system is programmed to reconstruct an image from the acquired k-space data, the reconstructed image having an image contrast that is related to a density of the magnetic particles and to an amplitude of the electromagnetic drive field.

11. The MRI system as recited in claim 7 in which computer system is programmed to direct the drive field generator and the RF system to apply the electromagnetic drive field contemporaneously with the spin-locking electromagnetic field.

12. The MRI system as recited in claim 7 in which the drive field generator includes at least one of a solenoid and a shielded solenoid.

13. The MRI system as recited in claim 12 in which the drive field generator includes an amplifier configured to drive the at least one of a solenoid and a shielded solenoid at the drive frequency.

14. The MRI system as recited in claim 7 in which the MRI system includes a gradient amplifier configured to drive the drive field generator.

\* \* \* \* \*